(12) United States Patent
Pericé et al.

(10) Patent No.: US 6,409,767 B1
(45) Date of Patent: Jun. 25, 2002

(54) ANKLE PROSTHESIS

(75) Inventors: Ramon Viladot Pericé, Barcelona (ES); Greta Dereymaeker, Oud-Heverlee (BE); Patrice Franåois Diebold, Nancy (FR); Beat Hintermann, Rienen (CH)

(73) Assignee: European Foot Platform, Nancy (FR)

( * ) Notice: Subject to any disclaimer, the term of this patent is extended or adjusted under 35 U.S.C. 154(b) by 0 days.

(21) Appl. No.: 09/704,765

(22) Filed: Nov. 3, 2000

(30) Foreign Application Priority Data

Nov. 5, 1999 (FR) .............................. 99 14198

(51) Int. Cl.[7] .................................................. A61F 2/42
(52) U.S. Cl. .................................................. 623/21.18
(58) Field of Search ........................ 623/21.11, 21.18, 623/18.11

(56) References Cited

U.S. PATENT DOCUMENTS

| 3,839,742 | A | * | 10/1974 | Link .................. 623/21.18 |
| 3,872,519 | A | * | 3/1975 | Giannestras et al. ..... 623/21.18 |
| 3,886,599 | A | * | 6/1975 | Schlein .................. 623/21.18 |
| 4,069,518 | A | * | 1/1978 | Groth, Jr. et al. ........ 623/21.18 |
| 4,755,185 | A | | 7/1988 | Tarr |
| 5,326,365 | A | * | 7/1994 | Alvine .................. 623/21.18 |
| 5,824,106 | A | * | 10/1998 | Fournol .................. 623/21.18 |
| 5,951,604 | A | | 9/1999 | Scheker |

FOREIGN PATENT DOCUMENTS

| DE | 88 12 806.7 | 10/1988 |
| EP | 0 864 305 | 3/1998 |

* cited by examiner

Primary Examiner—Eduardo C. Robert
(74) Attorney, Agent, or Firm—Millen, White, Zelano & Branigan, P.C.

(57) ABSTRACT

The invention provides an ankle prosthesis for use in the field of orthopedic prostheses comprising a talus implant for implanting in or on the talus and a top element including a tibia implant for implanting in or on the base of the tibia. The top element and the talus implant being mounted to move relative to each other by friction on a contact interface so as to allow the ankle to move. The contact interface presents a friction surface that can be considered as being a fraction of a substantially frustoconical surface. When implanted, the substantially frustoconical surface is oriented so that its larger radius portion is directed substantially towards the outside of the ankle.

19 Claims, 5 Drawing Sheets

ANKLE PROSTHESIS

The present invention relates to the technical field of ankle prostheses for performing orthopedic treatment of the ankle joint by implementing prosthetic elements for restoring the anatomy of the ankle joint.

The present invention relates to an ankle prosthesis comprising a talus implant designed to be implanted in or on the talus or "ankle bone", and a top element including a tibia implant for implanting in or on the base of the tibia, said top element and the talus implant being mounted to move relative to each other with friction at a contact interface to allow movement of the ankle.

BACKGROUND OF THE INVENTION

It is already known to use ankle prostheses after traumatic injury that has led to partial or total damage to the joint space of the ankle, in order to restore the joint anatomy of the ankle, at least in part.

Thus, ankle prostheses are already known comprising two implants, namely a talus implant for implanting in or on the talus, and a tibia implant for implanting in or on the base of the tibia. These two elements are implanted in the bones of the patient and they have congruent surfaces that are shaped in such a manner that the friction surface between the two implants is substantially spherical.

Hinge prostheses having two elements of the above-mentioned type confer satisfactory freedom of movement to an ankle joint restored in that way. Nevertheless, such prostheses make it possible to reproduce only some of the freedoms of movement of the natural ankle joint since the friction surface between the two implants is very different from the ideal physiological shape of the natural ankle joint. Since this is a constrained system, it leads to the patient's capacity for movement being limited and gives rise to the element making up the prosthesis becoming detached at an increased rate.

That is why proposals have already been made to attempt to improve the freedom of ankle prosthesis movement by designing ankle prostheses having three elements, namely: a talus implant, a tibia implant, and an intermediate implant interposed between the tibia implant and the talus implant.

The intermediate implant is free to move between the other two implants and rests against the tibia implant. The contact area between the talus implant and the intermediate implant is generally constituted by a friction surface that is generally cylindrical or spherical in shape, as with two-element implants.

Consequently a three-element ankle prosthesis gives rise to greater freedom of movement for the ankle joint as restored in this way, thereby giving the patient the possibility of moving in a manner close to that allowed by the natural physiological shape of the ankle joint. Nevertheless, a three-element ankle prosthesis does not completely reproduce the natural physiological shape of the ankle joint. The natural operation of the ankle joint implies that the foot meets the ground laterally, followed by rolling of the foot which implies rotation that is directed progressively towards the inside of the foot. Consequently, the natural operation of the ankle is not restored by presently-known ankle prostheses.

Furthermore, presently-known ankle prostheses have locking means, e.g. studs, that are secured to the tibia implant so as to secure the implant to the tibia bone. Pressure cannot be applied while this implant is being implanted since the patient is prone. Thus, on first pressure against the ground, the tibia implant is pressed against the tibia bone giving rise to relative displacement between the tibia implant and the tibia bone. This displacement gives rise to high and uncontrolled levels of mechanical stress at the locking studs and the housings for receiving them, which can give rise to deformation or even to a risk of separation.

OBJECTS AND SUMMARY OF THE INVENTION

Consequently, the objects of the invention seek to propose a novel ankle prosthesis that does not present the drawbacks of the above-mentioned ankle prostheses and that reproduces as accurately as possible all of the displacement movements of the natural ankle joint.

Another object of the invention seeks to propose a novel ankle prosthesis that is particularly suited to reproducing the natural ankle joint by means of a three-implant prosthesis.

Another object of the invention seeks to propose a novel ankle prosthesis enabling good control to be obtained over the various relative movements of the implants constituting the prosthesis.

Another object of the invention seeks to propose an ankle prosthesis suitable for preventing or limiting the creation of any osteophyte impeding movement of the ankle.

Another object of the invention is to propose a novel ankle prosthesis suitable for improving the conditions under which the prosthesis is implanted and for preventing uncontrolled deformation of the implants after they have been implanted.

Upon further study of the specification and appended claims, further objects and advantages of this invention will become apparent to those skilled in the art.

The objects of the invention are achieved by means of an ankle prosthesis comprising a talus implant for implanting in or on the talus and a top element including a tibia implant for implanting in or on the base of the tibia, said top element and the talus implant being mounted to move relative to each other by friction on a contact interface so as to allow the ankle to move, wherein the contact interface presents a friction surface that can be considered as being a fraction of a substantially frustoconical surface, said surface being oriented so that its larger radius portion is directed substantially towards the outside of the ankle.

BRIEF DESCRIPTION OF THE DRAWINGS

Other objects and advantages of the invention are explained in detail in the light of the following description with reference to the accompanying drawings given purely by way of non-limiting illustration, and in which.

MORE DETAILED DESCRIPTION

FIGS. 1 to 8 show an ankle prosthesis in accordance with the invention comprising a talus implant 1 designed to be implanted in or on the talus of the ankle joint of a patient. The ankle prosthesis in accordance with the invention also comprises a top element 2 including a tibia implant 3 for implanting in or on the base of the tibia of a patient.

The top element 2 and the talus implant 1 are mounted to move relative to each other by friction on a contact interface 4 so as to allow the ankle to move.

Figure 1:
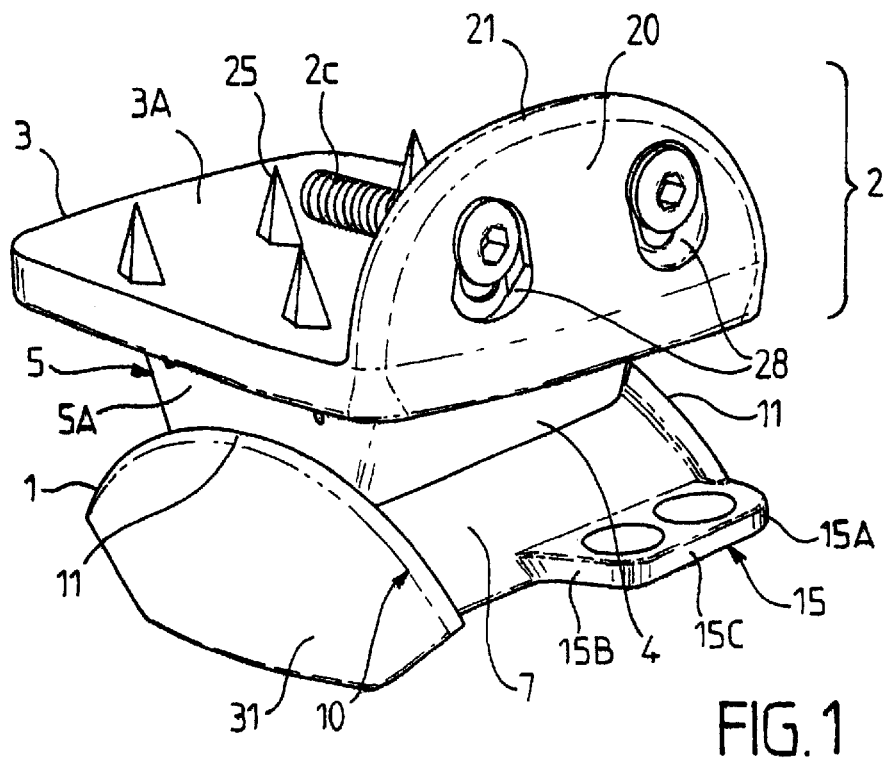
FIG. 1 is a three-quarters front perspective view of an embodiment of an ankle prosthesis in accordance with the invention.
Figure 2:
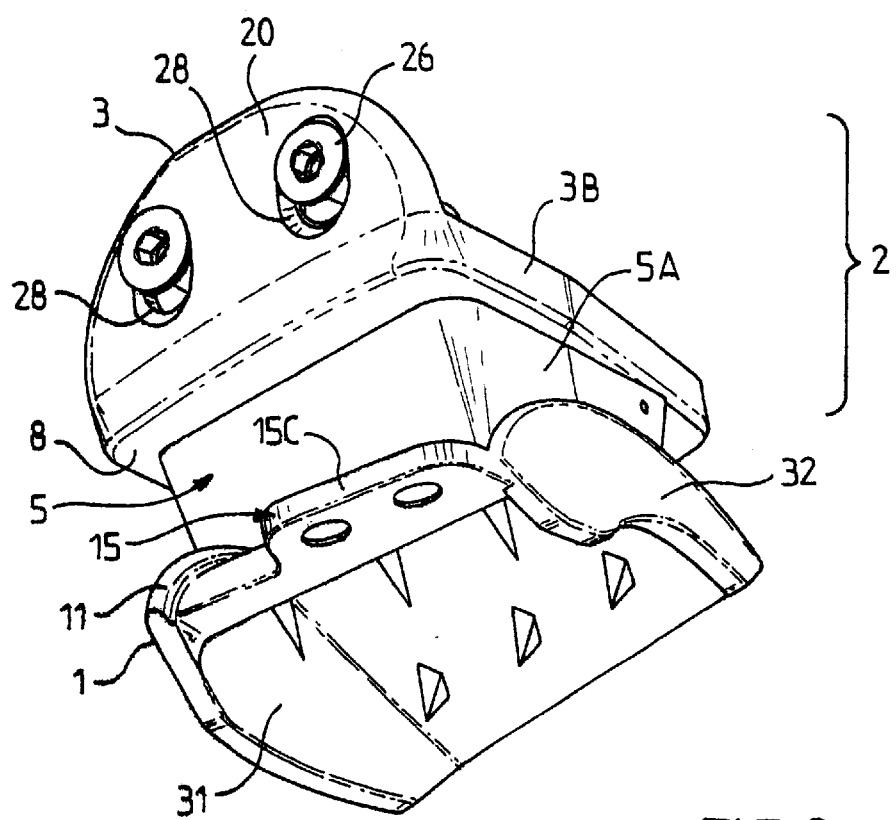
FIG. 2 is an inside front perspective view of an ankle prosthesis in accordance with the invention.

In the embodiment shown in FIGS. 1 and 2, the top element 2 further includes an intermediate implant 5 interposed between the tibia implant 3 and the talus implant 1, said intermediate implant 5 being in free frictional contact with the other two implants via each of two opposite faces.

Thus, in the description below, reference is constantly made to an ankle prosthesis comprising a set of three implants, namely: a talus implant 1; a tibia implant 3; and an intermediate implant 5; it being understood that the ankle implant of the invention is under no circumstances limited to a three-implant ankle prosthesis. Without going beyond the ambit of the invention, the ankle prosthesis could be made up of a set of two implants, namely: a talus implant 1; and a top element 2 constituted solely by a tibia implant 3. In this variant embodiment (see FIG. 6), the tibia implant 3 comes directly into contact with the talus implant 1 via a common contact interface 4.

Thus, the contact interface between the top element 2 and the talus implant 1 presents a friction surface that can be considered as forming a fraction of a substantially frustoconical surface 7 (FIG. 5), said surface being oriented so that its portion of larger radius R is directed substantially towards the outside of the ankle, i.e. away from the median axis of the body, when the prosthesis is in place. The friction surface is thus defined in three dimensions by a set of rectilinear generator lines having a single convergence point so as to form a surface that is substantially frustoconical. This leaves the various parts of the prosthesis completely free to move in three dimensions without relying on any mechanical constraint between said parts and/or the tissues of the ankle.

In the preferred application to three-component ankle prostheses as shown in FIGS. 1 to 4, the intermediate implant 5 is thus free to move with friction relative to the talus implant 1 over a portion of a frustoconical surface 7 having radii that vary from R to r, thus making it possible to move the foot outwards in dorsal flexion and conversely inwards in flexion towards the sole. By means of this feature of the joint surface, the ankle prosthesis of the invention makes it possible to follow very closely the natural physiological form of ankle joint displacement.

Figure 5:
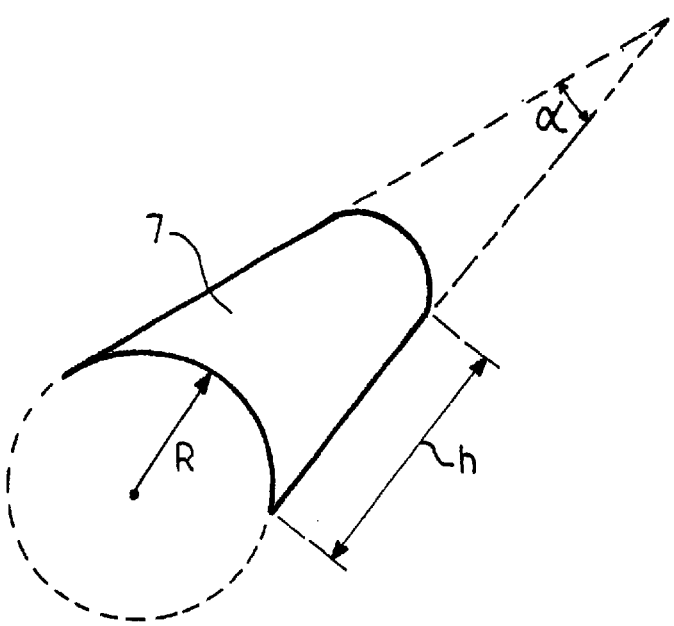
FIG. 5 is a diagrammatic projection showing the preferred configuration of an implementation detail of a prosthesis in accordance with the invention.
Figure 6:
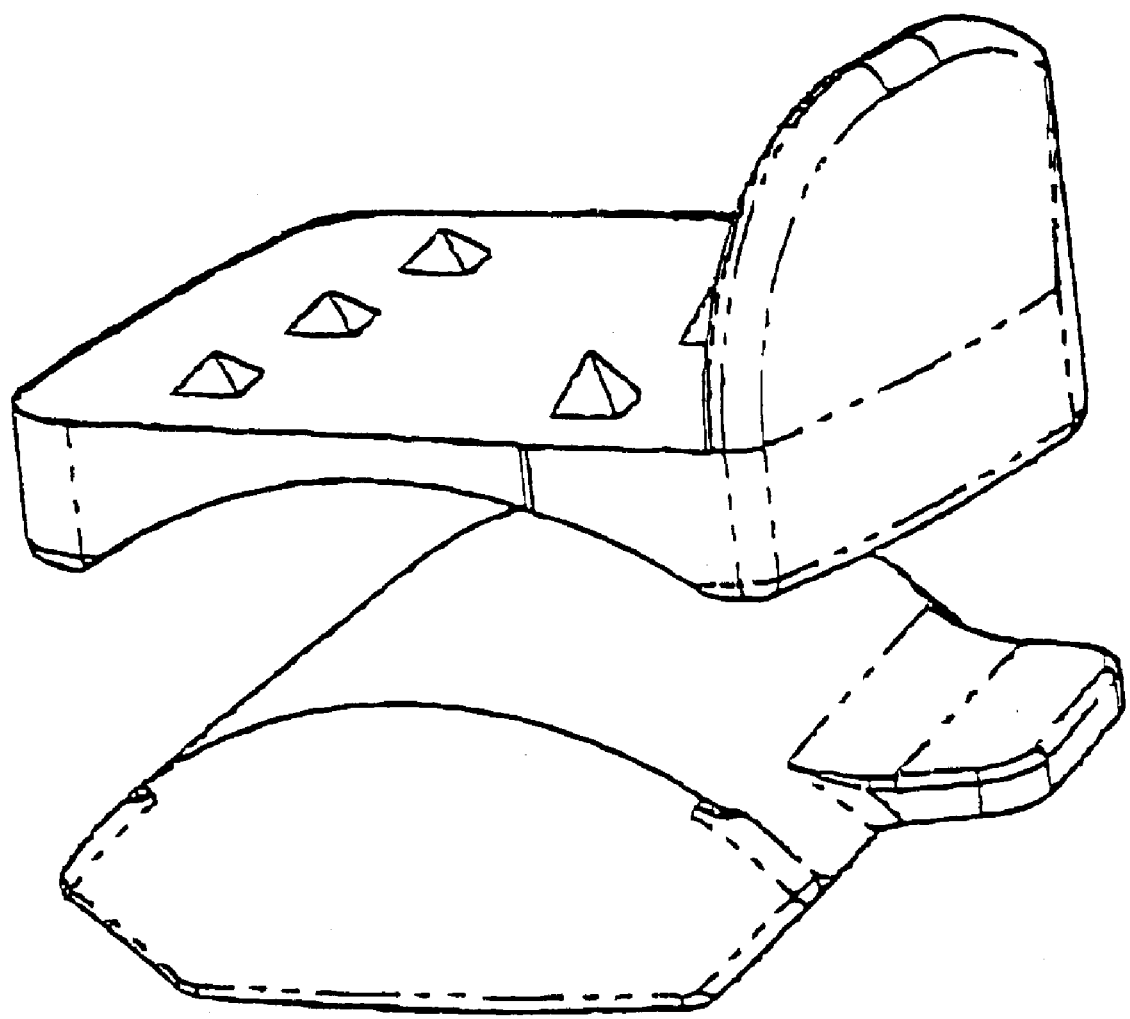
FIG. 6 is a side view of a two implant embodiemnt of the ankle prosthesis in accordance with the invention.

In a preferred variant of the invention, as shown diagrammatically in FIG. 5, the value of the angle α at the apex of the virtual cone of which the substantially frustoconical surface forms a fraction lies in the range 10° to 35°, the outer radius R of the conical portion lying in the range 15 mm to 30 mm while the geometrical height h of the conical zone lies in the range 20 mm to 50 mm.

The tibia implant 3 and the talus implant 1 are advantageously made of a metal alloy, such as chromium cobalt or any other material that withstands wear and is biocompatible.

In the preferred versions of the invention shown in FIGS. 1 to 4, the intermediate implant 5, e.g. made of a plastics material such as high density polyethylene or of ceramic, is in the form of an irregular polygon having a plane top surface in sliding contact with the likewise plane bottom face 8 of the tibia implant 3. In this preferred embodiment, the relative friction surface between the top surface of the intermediate implant 5 and the bottom face 8 can thus be considered as being a plane and provides freedom of movement in said plane in two directions. In this same preferred embodiment, the intermediate implant 5 is in sliding contact with the fraction of a frustoconical surface 7 via a bottom face that is complementary in shape to the frustoconical surface 7, advantageously presenting a frustoconical concave shape of small radius r and large radius R. By having the concave face of the intermediate implant 5 and the convex face of the frustoconical surface 7 exactly complementary in shape and dimensions, the ankle is completely free to move without constraint.

In the preferred embodiments shown in FIGS. 1 to 4, the substantially frustoconical surface fraction 7 forms the external contact surface of the talus implant 1 and is convex, in which case the bottom face of the intermediate implant 5 is concave. In a variant embodiment (see FIG. 8), an inverse mechanical disposition could be envisaged without thereby going beyond the ambit of the invention, the bottom face of the intermediate implant 5 then being convex while the outer contact surface of the talus implant 1 is concave.

Advantageously, the substantially frustoconical surface fraction 7 has guide means 10 on its outer surface to guide the displacement of the intermediate implant 5 and extending in a direction that is substantially normal to the axis of symmetry S of said surface 7. In this way, the intermediate implant 5 and the tibia implant 3 are constrained to follow displacement in three dimensions that is substantially normal to the generator lines of the truncated cone of which the substantially frustoconical surface 7 constitutes a fraction.

Advantageously, the guide means 10 are formed by at least one and preferably two parallel ribs 11 projecting from the substantially frustoconical surface 7 in order to engage the side flanks 5A of the intermediate implant 5.

Because of the presence of parallel ribs 11, the side flanks 5A of the intermediate implant 5 are guided by bearing against said ribs 11 during the displacement of the fraction of the substantially frustoconical friction surface 7.

Figure 7:
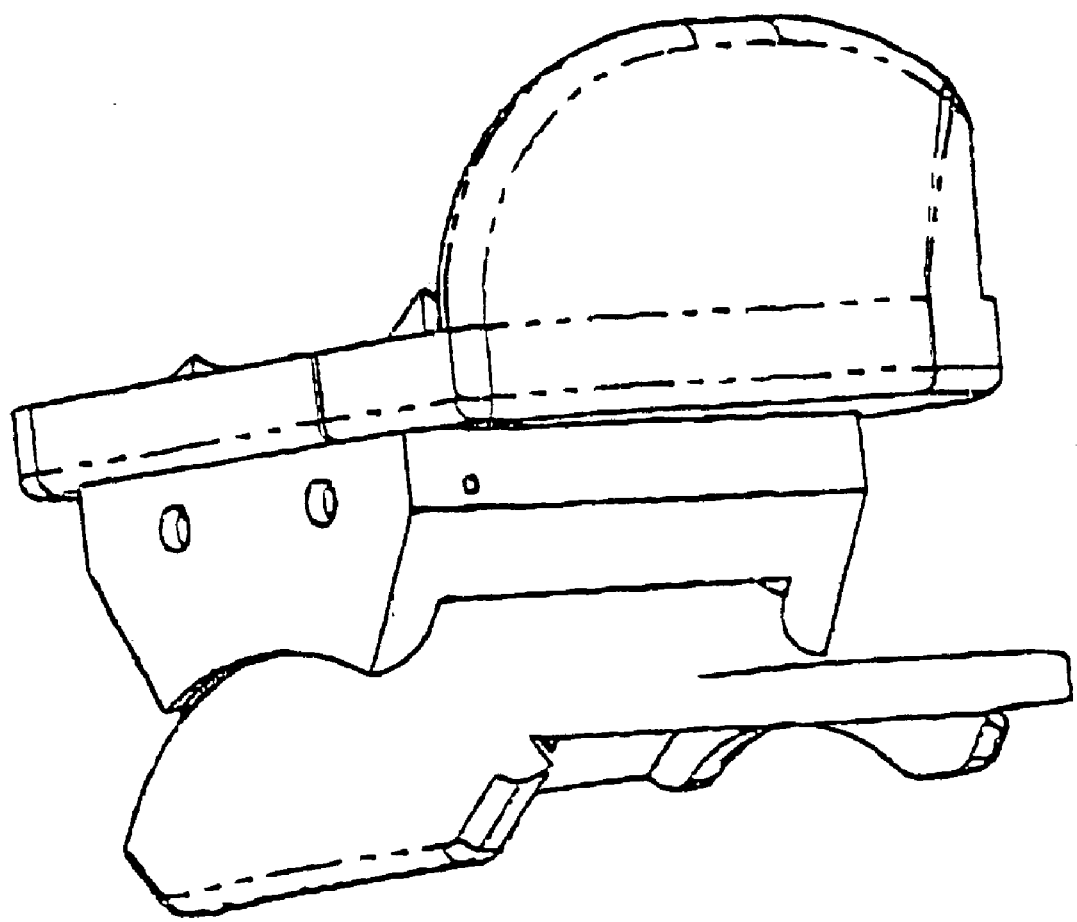
FIG. 7 is a variant of the prosthesis of the invention wherein guide means extend downwards from the intermediate implant.
Figure 8:
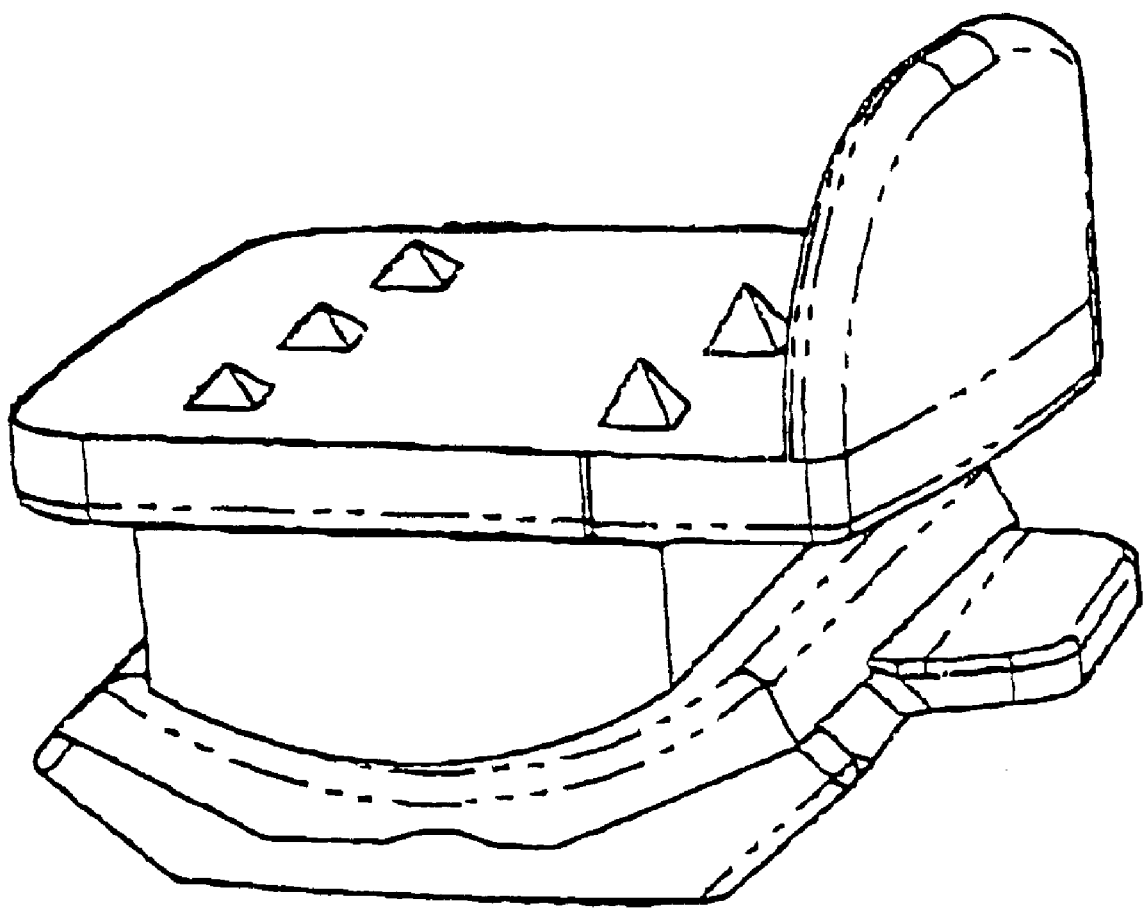
FIG. 8 is a side view of a variant of the ankle prosthesis of the invention wherein the talus implant has a concave outer contact surface.

In a variant shown in FIG. 7 the guide means 10 could be formed by two ribs 11 extending in parallel planes from the side flanks 5A of the intermediate implant 5, said ribs then bearing against and can be guided in two corresponding grooves formed in the body of the substantially frustoconical surface 7.

Advantageously, the ankle prosthesis in accordance with the invention has a talus implant 1 provided with an anterior talus shield 15 for protecting the ankle joint by preventing bone cells developing in the anterior portion of the ankle. Advantageously, the anterior talus shield 15 is formed as a substantially radial extension of the talus implant 1, from the anterior portion thereof. As shown in particular in FIG. 1, the anterior talus shield 15 extends from the anterior edge of said implant, extending the substantially frustoconical friction surface 7 substantially radially relative to the axis of symmetry S of the truncated cone in question.

Advantageously, in order to accommodate the natural asymmetry of the outline of the talus bone onto which the talus implant 1 is to be fitted, the anterior talus shield 15 extends radially in asymmetrical manner. To this end, and as shown in FIG. 1, the length of the lateral interior edge 15B is longer than the length of the lateral exterior edge 15A so as to form a front edge 15C that is oblique.

Advantageously, the tibia implant 3 is likewise provided with an anterior tibia shield 20 for protecting the ankle joint against any development of bone cells that could occur in unwanted manner in the anterior zone of the ankle and that would impede free movement of the ankle joint.

Figure 3:
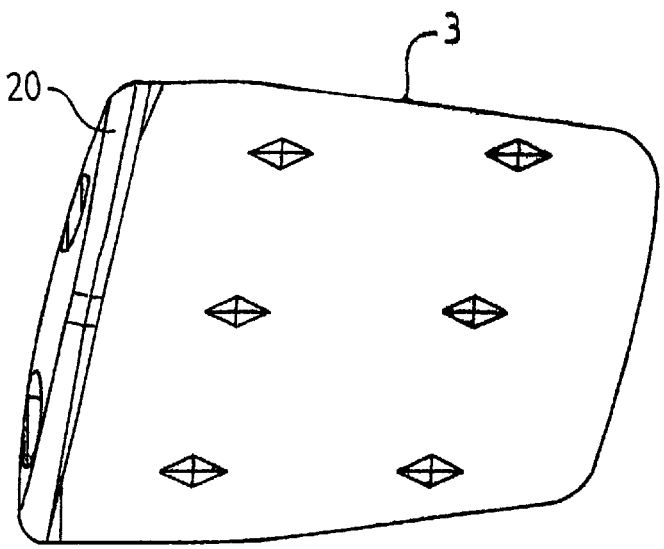
FIG. 3 is a plan view of an embodiment of the tibia implant.
Figure 4:
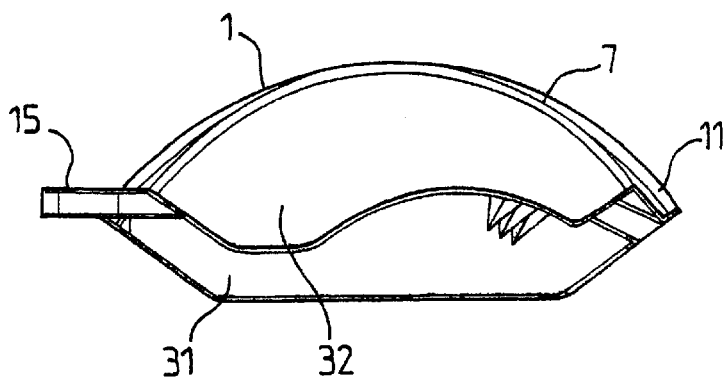
FIG. 4 is a side view showing a variant embodiment of a talus implant in accordance with the invention.

In a particularly advantageous version of the invention, the anterior tibia shield 20 is formed by an extension from the anterior edge of said implant, said extension extending upwards along the tibia bone when said implant is in place. Thus, as shown in FIGS. 1 to 3, the anterior tibia shield 20 extends from the top face 3A of the tibia implant 3 towards the tibia, extending in any plane, and for example in a plane perpendicular to the plane in which the face 3A extends. In a particularly advantageous variant of the invention (FIG. 3) the anterior tibia shield 20 matches the substantially circular arcuate shape of the distal portion of the tibia that is to rest on the face 3A. For this purpose, the anterior tibia shield 20 is of a complex asymmetrical shape, with the anterior edge of the plate of the tibia implant 3 being oblique and offset towards the median axis of the patient (FIG. 3).

As shown in FIG. 1, the anterior tibia shield 20 can have an anterior face that is substantially plane, provided with an outline that is substantially circular.

Advantageously, the talus implant 1 is defined in its two lateral zones by two flanges, respectively an outer flange 31 and an inner flange 32 for fitting over the concave bottom portion of the substantially frustoconical surface 7. The outer flange 31 preferably extends over a geometrical height that is greater than that of the inner flange 32.

As shown in particular in FIGS. 1 to 3, the tibia implant 3 is designed to be put into place by being pressed against the tibia bone. For this purpose, it includes a surface 3A forming a specially prepared plate, e.g. an irregular plate as shown in FIG. 3 and obtained by sand blasting. In a variant, the face 3A can be provided with spikes 25 (FIG. 1) so as to favor good fastening. The tibia implant 3 is put into place by inserting one or more screws 26 through appropriate holes formed in said tibia implant so as to fix the implant to the tibia bone.

In the invention, the anterior tibia shield 20 is provided with at least one through hole 28 for passing a fastening screw 26, said hole being larger in size than the section of the screw 26 so as to provide assembly clearance between the tibia implant 3 and the tibia. Advantageously, and as shown in FIGS. 1 and 2, the hole(s) 28 is/are oblong in shape. By means of this configuration, the tibia implant 3 can be installed under pressure without deforming the screws 26. The tibia implant 3 is put into place while the patient is prone, so complete compression of the tibia bone against the plate of the tibia implant 3 does not occur until the patient is standing. In the invention, the ability of the screws 26 to move relative to the oblong holes 28 allows natural locking to occur under pressure without damaging the screws 26 or the anterior tibia shield 20, because of the clearance between these two items.

The ankle prosthesis of the invention consequently makes it possible to reproduce faithfully the relative displacements that are possible in a natural ankle joint because of the existence of a substantially frustoconical friction surface between the talus implant 1 and the intermediate implant 5. In addition, the ankle prosthesis of the invention is better seated and prevents any development of bone cells that could hinder free movement of the ankle. The ankle prosthesis of the invention can also be implanted without any risk of damaging the integrity of the elements making up the prosthesis.

The entire disclosure of all applications, patents and publications, cited above, and of corresponding French Application No. 99 14198, filed Nov. 5, 1999, is hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. An ankle prosthesis comprising:
   a talus implant for implanting in or on a talus and a top element having a tibia implant for implanting in or on the base of a tibia,
   said top element and said talus implant being mounted to move relative to each other by friction on a contact interface to allow movement,
   wherein said contact interface presents a friction surface having a shape which is a fraction of a substantially frustoconical surface, said friction surface being oriented so that its larger radius portion is directed substantially towards the outside of an ankle when the prosthesis is in place,
   wherein said top element further includes an intermediate implant, having two opposite faces, which is interposed between said tibia implant and said talus implant, said intermediate implant being in free contact by relative friction with said talus implant and said tibia implant via said two opposite faces, and
   wherein said intermediate implant is in sliding contact with said tibia implant via a plane top face, and in sliding contact with said fraction of a substantially frustoconical surface via a bottom face having a shape which is complementary to said fraction of a substantially frustoconical surface.

2. An ankle prosthesis according to claim 1, wherein angle $\alpha$ at the apex of a virtual cone incorporating said fraction of a substantially frustoconical surface is 10° to 35°, larger radius R of said fraction of a frustoconical surface is 15 mm to 30 mm, and geometrical height h of said fraction of a frustoconical surface is 20 mm to 50 mm.

3. An ankle prosthesis according to claim 1, wherein said fraction of a substantially frustoconical surface forms an outer contact surface of said talus implant and is convex.

4. An ankle prosthesis according to claim 1, wherein said fraction of a substantially frustoconical surface forms an outer contact surface of said talus implant and is convex.

5. An ankle prosthesis according to claim 1, wherein said fraction of a substantially frustoconical surface has an axis of symmetry and includes guide means on its surface for guiding the displacement of said intermediate implant, said guide means extending in a direction that is substantially normal to the axis of symmetry of said fraction of a substantially frustoconical surface.

6. An ankle prosthesis according to claim 5, wherein said guide means is formed by two ribs extending from said fraction of a substantially frustoconical surface.

7. An ankle prosthesis according to claim 1, wherein said talus implant is provided with an anterior talus shield.

8. An ankle prosthesis according to claim 7, wherein said anterior talus shield has an anterior edge and said anterior talus shield is formed by a substantially radial extension of said talus implant, extending from the anterior edge of said talus implant.

9. An ankle prosthesis according to claim 7, wherein said anterior talus shield extends radially in asymmetrical manner whereby its interior lateral edge is longer than its exterior lateral edge.

10. An ankle prosthesis according to claim 7, wherein said tibia implant is provided with an anterior tibia shield.

11. An ankle prosthesis according to claim 1, wherein said tibia implant is provided with an anterior tibia shield.

12. An ankle prosthesis according to claim 11, wherein said tibia implant has an anterior edge and said anterior tibia shield is formed by an extension from the anterior edge of said tibia implant, said extension extending upwards towards a tibia when said tibia implant is in place.

13. An ankle prosthesis according to claim 11, wherein said anterior tibia shield is provided with at least one through hole for receiving a screw for securing said tibia implant, said through hole being of greater dimensions than a section of the screw inserted therein to provide assembly clearance between said tibia implant and a tibia.

14. An ankle prosthesis according to claim 13, wherein the at least one through hole is oblong in shape.

15. In a method of reconstructing a patient's ankle comprising implanting an ankle prosthesis, the improvement wherein an ankle prosthesis according to claim 1 is implanted.

16. An ankle prosthesis comprising:
a talus implant having means for implanting, means for attaching the talus implant in or on the base of a talus, or having both means for implanting and means for attaching the talus implant; and
a tibia implant having a top planar surface and means for implanting the tibia implant in or on the base of a tibia means for attaching the tibia implant in or on the base of a tibia or means for both implanting and attaching the tibia implant in or on the base of a tibia;
wherein said talus implant and said tibia implant are movable relative to each other by friction at a contact interface, said contact interface having a friction surface which is in the shape of a fraction of a substantially frustoconical surface, and
an intermediate implant having a top planar face in frictional contact with said tibia implant, and wherein said intermediate implant and said talus implant contact one another at said contact interface.

17. A prosthesis according to claim 16, wherein said talus implant and said tibia implant contact one another at said contact interface.

18. An ankle prosthesis comprising:
a talus implant for implanting in or on a talus and a top element having a tibia implant for implanting in or on the base of a tibia,
said top element and said talus implant being mounted to move relative to each other by friction on a contact interface to allow movement,
wherein said contact interface presents a friction surface having a shape which is a fraction of a substantially frustoconical surface, said friction surface being oriented so that its larger radius portion is directed substantially towards the outside of an ankle when the prosthesis is in place,
wherein said top element further includes an intermediate implant, having two opposite faces, which is interposed between said tibia implant and said talus implant, said intermediate implant being in free contact by relative friction with said talus implant and said tibia implant via said two opposite faces, and
wherein said fraction of a substantially frustoconical surface has an axis of symmetry and includes guide means on its surface for guiding the displacement of said intermediate implant, said guide means extending in a direction that is substantially normal to the axis of symmetry of said fraction of a substantially frustoconical surface.

19. An ankle prosthesis comprising:
a talus implant for implanting in or on a talus and a top element having a tibia implant for implanting in or on the base of a tibia,
said top element and said talus implant being mounted to move relative to each other by friction on a contact interface to allow movement.
wherein said contact interface presents a friction surface having a shape which is a fraction of a substantially frustoconical surface, said friction surface being oriented so that its large radius portion is directed substantially towards the outside of an ankle when the prosthesis is in place, and
wherein said tibia implant is provided with an anterior tibia shield.

* * * * *

UNITED STATES PATENT AND TRADEMARK OFFICE
CERTIFICATE OF CORRECTION

PATENT NO. : 6,409,767 B1
DATED : June 25, 2002
INVENTOR(S) : Ramon Viladot Pericé et al.

It is certified that error appears in the above-identified patent and that said Letters Patent is hereby corrected as shown below:

Title page,
Item [75], Inventors, "Franåois" should read -- François --.

Column 7,
Line 29, "base of a tibia" should read -- base of a tibia, --.
Line 31, "of a tibia or means" should read -- of a tibia, or means --.
Lines 38-42, delete ",and an intermediate implant having a top planar face in frictional contact with said tibia implant, and wherein said intermediate implant and said talus implant contact one another at said contact interface".

Column 8,
Line 39, "large radius portion" should read -- larger radius portion --.

Signed and Sealed this

Twenty-eighth Day of March, 2006

JON W. DUDAS
*Director of the United States Patent and Trademark Office*

UNITED STATES PATENT AND TRADEMARK OFFICE

(12) CERTIFICATE EXTENDING PATENT TERM
UNDER 35 U.S.C. § 156

| | | | |
|---|---|---|---|
| (68) | PATENT NO. | : | 6,409,767 |
| (45) | ISSUED | : | June 25, 2002 |
| (75) | INVENTOR | : | Pericé et al. |
| (73) | PATENT OWNER | : | European Foot Platform, S.C. |
| (95) | PRODUCT | : | Hintermann Series H3® Total Ankle Replacement System |

This is to certify that an application under 35 U.S.C. § 156 has been filed in the United States Patent and Trademark Office, requesting extension of the term of U.S. Patent No. 6,409,767 based upon the regulatory review of the product Hintermann Series H3® Total Ankle Replacement System by the Food and Drug Administration. According to United States Patent and Trademark Office records, the original expiration date of the patent as of the date of issuance of this certificate is November 3, 2020. Because it appears that the requirements of the law have been met, this certificate extends the term of the patent for the period of

(94) 5 years subject to the payment of maintenance fees as provided by law, with all rights pertaining thereto as provided by 35 U.S.C. § 156.

I have caused the seal of the United States Patent and Trademark Office to be affixed this 6th day of October 2022.

Katherine K. Vidal
Under Secretary of Commerce for Intellectual Property and Director of the United States Patent and Trademark Office